United States Patent [19]

Takeda et al.

[11] Patent Number: 5,043,351

[45] Date of Patent: Aug. 27, 1991

[54] HYGROSCOPIC INSECT-PROOFING COMPOSITION

[75] Inventors: Mutsuhiko Takeda, Tokyo; Minoru Kakuda, Matsudo; Masafumi Shimpo, Kashiwa; Kiyoshi Yoshida, Tokyo, all of Japan

[73] Assignee: Mitsubishi Gas Chemical Company, Inc., Tokyo, Japan

[21] Appl. No.: 343,673

[22] Filed: Apr. 27, 1989

[30] Foreign Application Priority Data

Apr. 28, 1988 [JP] Japan ................................ 63-103768

[51] Int. Cl.$^5$ ...................... A01N 25/00; A01N 43/32
[52] U.S. Cl. ..................................... 514/452; 514/770
[58] Field of Search ................................ 514/770, 452

[56] References Cited

U.S. PATENT DOCUMENTS

| 3,917,814 | 11/1975 | Hedges et al. | 514/770 |
| 4,632,936 | 12/1986 | Boase et al. | 514/770 |

FOREIGN PATENT DOCUMENTS

| 1619865 | 10/1977 | Fed. Rep. of Germany | 514/770 |
| 115802 | 4/1988 | Japan . | |

*Primary Examiner*—Allen J. Robinson
*Attorney, Agent, or Firm*—Sherman and Shalloway

[57] ABSTRACT

Disclosed is a hygroscopic insect-proofing composition, and more particularly a trioxane-containing composition which is useful in insect-proofing and damp proofing of clothing.

5 Claims, No Drawings

HYGROSCOPIC INSECT-PROOFING COMPOSITION

BACKGROUND OF THE INVENTION

1. Field of the Invention

The present invention relates to a hygroscopic insect-proofing composition, and more particularly to a trioxane-containing composition which is useful in insect-proofing and damp proofing of clothing.

2. Description of the Related Art

Sublimable substances such as camphor, naphthalene and p-dichlorobenzene have been used as insect-proofing agents for clothing.

These conventional sublimable substances have the defect of giving off peculiar inherent irritating odors which remain in clothing after storage. Camphor and naphthalene have a weak action on clothing harmful insects such as case-making clothes moth (*Tinea pellionella* Linne) and various carpet beetles such as *Attagenus piceus* Oliv and *Authrenus verbasci* Linne. p-Dichlorobenzene has toxicity and causes environmental pollution.

The present inventors previously developed a sublimable insect-proofing agent comprising 1,3,5-trioxane (hereinafter called "trioxane") as an active ingredient (Japanese Laid-Open Patent Publication No. 115802/1988). The insect-proofing agent gives off only slight odor, which will disappear from clothing immediately after storage.

Thrioxane is a solid substance having a flash point of 40° C. (as measured by a Setaflash ® Closed-Cup Apparatus in accordance with ASTM) and hence will never happen to give off sufficient vapor to flash, as long as it is used in ordinary manner as a home insect-proofing agent. But it is not guaranteed that trioxane is free from the risk of flashing in the atmosphere of abnormally high temperature or in the presence of a flame source. Therefore, it is desirable to have an increased flash point by mixing trioxane with another substance.

Another common problem encountered when storing clothing is that the clothing would be subject to an undesirable phenomenon such as getting musty in the atmosphere of high humidity. Heretofore, various hygroscopic agents have been used in order to eliminate this problem.

Consequently, both an insect-proofing agent and a hygroscopic agent are necessary at the same time for problem-free storage of clothing. In that case, a number of tablets (balls or otherwise shaped bodies) of insect-proofing agent and a number of tablets (balls or otherwise shaped bodies) of hygroscopic agent must be placed individually here and there in a wardrobe or a dresser, which is laborious and time-consuming.

SUMMARY OF THE INVENTION

The present inventors have made various researches on a composition which is insect-proofing and hygroscopic and which has an increased flash point. To this result, the inventors have selected silica gel out of various kinds of absorptive carriers and have occluded trioxane in the carrier to provide a new composition. The inventors have found the new composition fit for their purpose.

It is accordingly an object of the present invention to provide a hygroscopic insect-proofing composition which has a high flash point and which prevents clothing from being damaged by harmful insects and, at the same time, desiccates, guaranteeing an insect-proofing performance for a long time.

Another object of the invention is to provide a hygroscopic insect-proofing composition which can keep up an excellent degree of insect-proofing performance and also an adequate moisture-absorbing ability. And the composition is easy to use and handle.

Still another object of the invention is to provide a hygroscopic insect-proofing composition comprising 1,3,5-trioxane occluded in silica gel.

A further object of the invention is to provide a hygroscopic insect-proofing composition in which a mixture of 1,3,5-trioxane and a stabilizing agent of 0.05 to 10% by weight per the amount of trioxane is occluded in silica gel.

DETAILED DESCRIPTION OF THE PREFERRED EMBODIMENTS

The present invention is based on a discovery that silica gel, out of various kinds of absorptive carriers, as it supports trioxane, exceptionally elevates the flash point of trioxane and serves to keep up the insect-proofing action of trioxane. Conventionally, many other absorptive carriers are known, for example, active alumina, zeolite, diatomaceous earth and various silicate. However, as described in Examples and Comparative Examples below, when trioxane was supported by most of the individual absorptive carriers other than silica gel, no increase of the flash point was found; on the contrary, when trioxane was supported by silica gel, a remarkable increase of the flash point was found. Further, since it can retard the volatizing speed of trioxane, silica gel is excellent in keeping up the insect-proofing action of trioxane.

Silica gel to be used in the present invention is very porous non-crystalline anhydrous silicic acid. Its properties, though depend on the manufacturing process and other factors, are generally preferred that the BET specific surface is in the range of 300 to 1,000 $m^2$/g, and the pore volume is in the range of 0.2 to 1.0 cc/g. In general, silica gel used as a desiccating agent is available with ease. Silica gel in the form of unshaped powder, granules, or otherwise shaped bodies such as spherical, cylindrical or cubic ones, having a particle diameter of 0.1 to 10 mm, especially 0.5 to 5 mm, is suitable for use. Also, silica gel in which cobalt chloride, as a moisture indicator, is previously contained may be used.

1,3,5-Trioxane is a sublimable solid substance of the chemical formula $(CH_2O)_3$ having a melting point of 64° C. and stable at room temperature in air.

Since a small amount of formaldehyde may be evoluted from the composition of the present invention, it is preferred to add a stabilizer, e.g. urea, a hydrazine derivative such as isonicotinic acid hydrazide and/or oximes such as cyclohexanone oxime. The preferred amount of the stabilizer is 0.05 to 10% by weight, especially 0.1 to 3% by weight per the amount of trioxane.

The proportions of trioxane and silica gel in the composition of the present invention can be varied over a wide range. Generally, on a two-component basis, the composition of the invention contains 5 to 50% by weight, especially 10 to 45% by weight, of silica gel.

The preparation of the composition of the present invention is not limited to a specific method. For example, the Composition of the invention may be prepared by: a) stirring and mixing a liquid of molten trioxane and silica gel; and b) by mixing a solid of trioxane and silica gel to occlude the gasified trioxane in silica gel. In the composition of the invention, stabilizers and/or additives such as perfumes and lubricants may be incorporated, as desired. The incorporation of these stabilizers and/or additives is not limited to a specific method; for example, the stabilizers and/or additives may be previously incorporated in trioxane and/or silica gel.

The composition of the present invention produces trioxane vapor which shows excellent insect-proofing action virtually equal to the action of trioxane alone. This insect-proofing action is substantially equal to that of p-dichlorobenzene and is superior to naphthalene and camphor. Further, since its gasifying speed is retarded, trioxane in the composition of the present invention is excellent in keeping up the insect-proofing action.

The composition of the invention also shows the moisture absorbing action equal to that of silica gel alone. After the composition has absorbed water, its insect-proofing action cannot be reduced.

The composition of the invention is high in flash point, compared with trioxane alone and also with the composition in which instead of silica gel, an alternative absorptive carrier such as active alumina, zeolite or cellulose is used.

The composition of the present invention may be wrapped in a film so that both the trioxane gasifying rate and the moisture absorbing rate of the composition can be controlled.

Since characteristics of the composition of the present invention substantially remains even after the composition has absorbed moisture, it is unnecessary to consider disposing of the moisture-absorbed composition as well as conventional silica gel.

The following examples illustrate the present invention more specifically.

EXAMPLE 1

12 grams of a mixture of trioxane and cyclohexanone oxime (content: 1% by weight) were put in a nitrogen-substituted 200 ml. three-neck flask, and were melted on a hot oil bath, with stirring, until the temperature increased to 65° C. 18 grams of powdery silica gel (BET specific surface 450 $m^2/g$, pore volume 0.8 cc/g, particle diameter 0.15 mm) were admixed to the mixture, and the resulting composition was mildly stirred for one hour at 65° C., whereupon the composition was cooled to form a hygroscopic insect-proofing composition.

This composition thus prepared was used in the following insect-proofing test. Two grams of the composition was put on the bottom of a 900 ml. glass bottle. A metallic cage having a diameter of 3 cm containing ten 35-day-old larvae of case-making clothes moth (*Tinea pellionella* Linne) and square pieces of woollen fabrics each side measuring 2 cm was fixed to a position 5 cm above the composition. The bottle was then sealed up and was left to stand in a constant-temperature chamber at 30° C. for 24 hours. Then the cage was taken out, whereupon the mortality of the case-making clothes moth larvae and the amount of feeding damage to the woollen fabrics (weight loss) were examined. The results are shown in Table 1.

EXAMPLE 2

Nine grams of a mixture of trioxane and urea (content: 0.6% by weight), and 21 grams of a mixture of spherical silica gel (BET specific surface 650 $m^2/g$, pore volume 0.36 cc/g, particle diameter 2-4 mm)) and cyclohexanone oxime (content: 1% by weight) were put in a nitrogen-substituted 200 ml. Kjeldahl flask, and were mixed by a rotary evaporator for one hour at 65° C., whereupon the resulting composition was cooled to form a hygroscopic insect-proofing composition. The composition thus prepared was used in the same insect-proofing assay as in Example 1. The results are shown in Table 1.

EXAMPLE 3

4.5 grams of a mixture of trioxane and isonicotinic acid hydrazine (content: 0.1% by weight), and 25.5 grams of granular silica gel (BET specific surface 850 $m^2/g$, pore volume 0.25 cc/g, particle diameter 5-10 mm) were put in a nitrogen-substituted 200 ml. Kjeldahl flask, and were mixed by a rotary evaporator for 2 hours at 40° C., whereupon the resulting composition was cooled to form a hygroscopic insect-proofing composition. The composition thus prepared was used in the same insect-proofing assay as in Example 1. The results are shown in Table 1.

COMPARATIVE EXAMPLES 1-4

The same insect-proofing test as in Example 1 was conducted on each of: a tablet (2 grams) of trioxane; a tablet (2 grams) of p-dichlorobenzene (commercially available insect-proofing agent); a tablet (2 grams) of naphthalene (commercially available insect-proofing agent); and no insect-proofing agent. The results are shown in Table 1.

TABLE 1

| Example No. | Insect-proofing agent | Death number | Amount of feeding (mg) |
| --- | --- | --- | --- |
| 1 | trioxane/silica gel (powder) (weight ratio; 40/60) | 10 | 0.3 |
| 2 | trioxane/silica gel (spherical) (weight ratio; 30/70) | 10 | 0.5 |
| 3 | trioxane/silica gel (granular) (weight ratio; 15/85) | 10 | 0.6 |
| Comparative Example 1 | trioxane | 10 | 0.2 |
| Comparative Example 2 | p-dichlorobenzene | 10 | 0.4 |
| Comparative Example 3 | naphthalene | 2 | 3.5 |
| Comparative Example 4 | none | 0 | 6.5 |

EXAMPLE 4

20 grams of the composition (trioxane:spherical silica gel=3:7 weight ratio) prepared in Example 2 were left deposited in a container which was maintained at a constant temperature of 30° C. and at a constant humidity of 80%. 24 hours later, the amount of absorbed water in the composition was measured, and as a result, the composition was found to have adsorbed 1.24 grams of water.

COMPARATIVE EXAMPLE 5

14 grams of the same spherical silica gel as used in Example 2 were left deposited in a container which was maintained at a constant temperature of 30° C. and a constant humidity of 80%. 24 hours later, the amount of water absorbed in the composition was measured, and as a result, the composition was found to have absorbed 1.22 grams of water.

EXAMPLES 5-7 AND COMPARATIVE EXAMPLE 6

The flash point of each of the compositions prepared in Examples 1-3 and the flash point of trioxane alone were measured using Setaflash ® Closed-Cup Apparatus in accordance with ASTM. The results are shown in Table 2.

COMPARATIVE EXAMPLES 7-11

Using nine grams of trioxane and 21 grams of a hygroscopic carrier, a composition was prepared in the same process as was in Example 2. The experiment was repeated to prepare several compositions; for the hygroscopic carrier, active alumina, zeolite, calcium silicate, diatomaceous earth and cellulose were used one in each composition. The flash points of the individual compositions were measured using Setaflash ® Closed-Cup Apparatus in accordance with ASTM. The results are shown in Table 3.

TABLE 2

| Example No. | Composition | Flash point (°C.) |
| --- | --- | --- |
| 5 | trioxane/silica gel (powder) (weight ratio; 40/60) | 45 |
| 6 | trioxane/silica gel (spherical) (weight ratio; 30/70) | 52 |
| 7 | trioxane/silica gel (granular) (weight ratio; 15/85) | 60 |
| Comparative Example 6 | trioxane alone | 40 |

TABLE 3

| Comparative Example No. | Composition | Flash point (°C.) |
| --- | --- | --- |
| 7 | trioxane/active alumina | 40 |
| 8 | trioxane/zeolite | 40 |
| 9 | trioxane/calcium silicate | 40 |
| 10 | trioxane/diatomaceous earth | 40 |
| 11 | trioxane/cellulose | 40 |

What is claimed is:

1. A hygroscopic insect-proofing composition comprising a silica gel and 1,3,5-trioxane occluded in the silica gel, wherein on a two-component basis, the composition contains 5 to 50% by weight of trioxane and 50 to 95% by weight of silica gel.

2. A hygroscopic insect-proofing composition according to claim 1, wherein on a two-component basis, the composition contains 10 to 45% by weight of trioxane and 55 to 90% by weight of silica gel.

3. A hygroscopic insect-proofing composition according to claim 1, wherein the silica gel has a particle diameter of 0.1 to 10 mm.

4. A hygroscopic insect-proofing composition, comprising;
   50 to 95% by weight of silica gel; and
   5 to 50% by weight of a mixture of 1,3,5-trioxane and 0.05 to 10% by weight, based on the trioxane, of a stabilizer, the mixture being occluded in the silica gel.

5. A hygroscopic insect-proofing composition according to claim 4 wherein the stabilizer is present in an amount of 0.01 to 3% by weight, based on the trioxane.

* * * * *